United States Patent [19]

Quinlan

[11] 4,080,375

[45] Mar. 21, 1978

[54] METHYLENE PHOSPHONATES OF AMINO-TERMINATED OXYALKYLATES AND USES THEREFOR

[75] Inventor: Patrick M. Quinlan, Webster Groves, Mo.

[73] Assignee: Petrolite Corporation, St. Louis, Mo.

[21] Appl. No.: 732,562

[22] Filed: Oct. 15, 1976

Related U.S. Application Data

[63] Continuation of Ser. No. 113,092, Feb. 5, 1971, abandoned.

[51] Int. Cl.$^2$ ............................ C07F 9/38; C02B 5/06
[52] U.S. Cl. .................................. 260/502.5; 210/58; 252/8.55 D; 252/180; 252/184
[58] Field of Search ...................................... 260/502.5

[56] References Cited

U.S. PATENT DOCUMENTS

| 2,673,214 | 3/1954 | Bersworth et al. ............... 260/502.5 |
| 2,961,311 | 11/1960 | Bersworth et al. ............... 260/502.5 |
| 3,288,846 | 11/1966 | Irani et al. ......................... 260/502.5 |
| 3,298,956 | 1/1967 | Irani et al. ......................... 260/502.5 |

FOREIGN PATENT DOCUMENTS

| 750,481 | 6/1956 | United Kingdom ............. 260/502.5 |
| 1,023,785 | 3/1966 | United Kingdom ............. 260/502.5 |

*Primary Examiner*—Joseph E. Evans
*Attorney, Agent, or Firm*—Sidney B. Ring; Hyman F. Glass

[57] ABSTRACT

Methylene phosphonates of amino-terminated oxyalkylates having at least two amino groups; and to uses therefor, particularly as scale inhibitors, chelating agents, etc.

9 Claims, No Drawings

METHYLENE PHOSPHONATES OF AMINO-TERMINATED OXYALKYLATES AND USES THEREFOR

This is a continuation of application Ser. No. 113,092 filed Feb. 5, 1971 now abandoned.

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

More than twenty-five years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which threshold active compounds sequester the cations of relatively insoluble compounds and the low concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffectiveness or less effective compounds.

A compound that has sequestering power does not predictably have threshold inhibiting properties. For example, ethylene diamine tetracetic acid salts are powerful sequesterants but have no threshold activities.

I have now discovered a process for inhibiting scale such as calcium, barium and magnesium carbonate, sulfate, silicate, etc., scale which comprises employing threshold amounts of methylene phosphonates of amino-terminated oxyalkylates having at least two amino groups.

As is well known, alkylene oxides can be reacted with various oxyalkylatable materials (i.e., materials which contain hydrogen atoms capable of reacting with a 1,2 alkylene oxide) to form polyalkylene oxide derivatives thereof. Thus, when an oxyalkylatable material of the formula $ZH_z$ is reacted with an alkylene oxide such as ethylene oxide, there is obtained a compound of the formula

such as

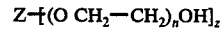

where $n$ is a number determined by the moles of alkylene oxide reacted and $z$ is a number determined by the compound's oxyalkylatable hydrogens.

Many polyalkylene oxide block polymers have been prepared containing definite homogeneous block units or segments of ethylene oxide, propylene oxide, butylene oxide, etc., such as disclosed in U.S. Pat. Nos. 2,674,619, 2,677,700 and elsewhere.

Where ethylene oxide is reacted with water, a polymeric polyethylene glycol of the type $H(OEt)_n$—O—$(EtO)_nH$ is formed. Similarly, where propylene oxide is reacted with water, a polymeric polypropylene glycol of the type $H(OPr)_n$—O—$(PrO)_nH$ is formed. When water is first reacted with ethylene oxide followed by reaction with propylene oxide, a polymer containing blocks of ethylene oxide units and blocks of propylene oxide are formed, $H(OPr)_m(OEt)_nO$—$(EtO)_n(PrO)_mH$, or when added in the reverse order the following block polymer is formed:

H(OEt)$_m$(OPr)$_n$O(PrO)$_n$(EtO)$_m$H

Block polymers of this type can be formed by adding infinite numbers of block units, for example, H(OPr)$_y$(OEt)$_x$(OPr)$_m$(OEt)$_n$—O—(EtO)$_n$(PrO)$_m$—(EtO)$_x$(PrO)$_y$H This block-wise or sequential addition could be continued infinitely. Since only two types of alkylene oxides are employed, these polymers are di-block polymers.

Where three or more different types of alkylene oxides are employed, ter-block polymers are formed as illustrated by sequentially adding ethylene oxide, propylene oxides, and butylene oxides to water to form:

H(OBu)$_x$(OPr)$_m$(OEt)$_n$—O—(EtO)$_n$(PrO)$_m$(BuO)$_x$H

These ter-block units may also be continued infinitely. Where, for example, other alkylene oxides are used in addition to ethylene, propylene, and butylene oxides, a higher type of block polymer is formed, such as when octylene oxide or styrene oxide are additionally reacted. It is to be noted that block units of these polymers within themselves are homogeneous units, i.e., each block is derived from a single alkylene oxide.

Polyalkylene oxides have also been propared by reacting mixtures of alkylene oxide such as when a mixture of ethylene oxide and propylene oxide are reacted. When this is done, a random or hetero-polymer is obtained. Thus, for example, where a 50/50 molar mixture of EtO and PrO are reacted when an oxyalkylatable material, such as water, one obtains a polymer having no orderly arrangement of the alkylene oxide units since the distribution of EtO and PrO units in the molecule is random may be designated by

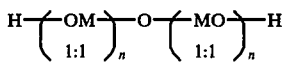

where MO represents a random distribution of EtO and PrO units, such as, for example, H(OPr)$_6$(OEt)$_2$(OPr)$_4$(OEt)$_2$(OPr)$_2$—O—
—(EtO)(PrO)(EtO)$_2$(PrO)$_3$(EtO)(PrO)H "MO" as employed herein refers to mixtures of ethylene oxide in conjunction with a hydrophobic alkylene oxide, i.e., an alkylene oxide having more than two carbon atoms. Thus, the hydrophobic alkylene oxides include propylene oxide, butylene oxide, amylene oxide, octylene oxide, styrene oxide, methylstyrene oxide, cyclohexane oxide, etc. However, in practice I prefer to employ ethylene oxide in conjunction with propylene and/or butylene oxide.

The alkylene oxides employed herein are 1,2-alkylene oxides of the formula

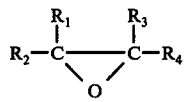

wherein $R_1$, $R_2$, $R_3$ and $R_4$ are selected from the group consisting of hydrogen, an aliphatic, cycloaliphatic, aryl, etc., group for example ethylene oxide, propylene oxide, butylene oxide, amylene oxide, octylene oxide, styrene oxide, methylstyrene oxide, cyclohexane oxide (where $R_1$ and $R_3$ are joined to make a ring), etc.

Equivalents of alkylene oxides can also be employed, for example alkylene carbonates, i.e., ethylene carbonate, propylene carbonate, butylene carbonate, etc. In addition, alkylene oxides of the glycide, methyl glycide type can also be employed.

For the sake of simplicity of presentation, the invention will be illustrated by employing as a base oxyalkylatable compound ZH$_z$ and by employing only ethylene, propylene, and butylene oxides with the understanding that other hydrophobe oxides can be used in place of propylene and butylene oxides such as amylene oxide, octylene oxide, styrene oxide, etc. By way of example Z may be one of the following:

(a) Polyhydric alcohols
  Ethylene glycol
  Propylene glycol
  Diethylene glycol
  Trimethylene glycol
  2,3-butanediol
  1,4-dihydroxy-2-butene
  1,12-dihydroxy octadecane
  1,4-dihydroxy cyclohexane
  2,2-dimethyl-1,3-propanediol
  2-ethyl-2-butyl propanediol-1,3
  Glycerol
  Erythritol
  Sorbitol
  Mannitol
  Inositol
  Trimethylol propane
  Pentaerythritol
  Polyallyl alcohol
  Bis (4-hydroxycyclohexyl) dimethyl methane
  1,4-dimethylol benzene
  4,4'-dimethylol diphenyl
  Dimethylol xylenes
  Dimethylol naphthalenes, etc.
(b) Polyhydric ether alcohols
  Diglycerol
  Triglycerol
  Dipentaerythritol
  Tripentaerythritol
  Dimethylolanisoles
  Beta hydroxyethyl ethers of polyhydric alcohols and phenols such as
    Diethylene glycol
    Polyethylene glycols
  Bis (beta hydroxyethyl ether) of hydroquinone
  Bis (beta hydroxyethyl ether) of bisphenol
  Beta hydroxyethyl ethers of glycerol, pentaerythritol, sorbitol, mannitol, etc.
  Condensates of alkylene oxides such as ethylene oxide; propylene oxide; butylene oxide; isobutylene oxide; glycidol; glycid ethers, etc., with polyhydric alcohols such as the foregoing.
(c) Polyhydric phenols
  Hydroquinone
  Resorcinol
  Pyrogallol
  Bisphenol (predominantly 4,4'-dihydroxy diphenyl dimethyl methane)
  Dihydroxy diaryl sulfones
(d) Phenol-aldehyde resins
  See U.S. Pat. No. 2,499,365

The amines employed herein are amino-terminated oxyalkylates, having at least two amino groups which may be described by the following general formula:

$$Z[(AO)_n-A-NH_2]_z$$

where Z is the oxyalkylated base, n defines the number of OA or oxyalkylene units in the molecule, A is an alkylene group and z the number of amino-terminated groups. n may be, for example, about 3 to 150 or more, such as from about 5 to 75, but preferably 8 to 75; z is a number such as, for example, from 2 to 5, or more, but preferably 2 to 3. In general, if the oxyalkylatable base is $H_2O$ $z = 2$; if glycerol or trimethylolethane $z = 3$; if pentaerythritol $z = 4$, etc. Preferably all the terminal oxyalkylated groups should be amine, but the compound should contain at least two terminal amino groups.

The hydroxy-terminated oxyalkylates may be converted to amino terminated oxyalkylates by known processes such as that described in Belgian Pat. No. 634,741 wherein the hydroxy-terminated oxyalkylates are reacted with ammonia and hydrogen in the presence of Raney Ni at high temperatures and pressures.

In general, the amino-terminated oxyalkylates are analogous to the corresponding OH terminated oxyalkylates wherein an amino group replaces the OH groups. The following table generally illustrates certain amino-terminated oxyalkylates of this invention.

TABLE I

Step I.
  (1) $Z[(EtO)_n NH_2]_z$
  (2) $Z[(PrO)_n NH_2]_z$
  (3) $Z[(BuO)_n NH_2]_z$
  (4) $Z[(MO)_n NH_2]_z$
  (5) $Z[(PrO\text{-}BuO)_n NH_2]_z$ Step II. — Reaction of the Step I product with one of the five oxides or mixtures employed in Step I, which oxide had not been reacted in the immediately preceding step. For example:
  (6) $Z[(EtO)_n(PrO)_m NH_2]_z$
  (7) $Z[(EtO)_n(BuO)_m NH_2]_z$
  (8) $Z[(EtO)_n(MO)_m NH_2]_z$
  (9) $Z[(EtO)_n(PrO\text{-}BuO)_m NH_2]_z$
  (10) $Z[(PrO)_n(EtO)_m NH_2]_z$
  (11) $Z[(PrO)_n(BuO)_m NH_2]_z$
  (12) $Z[(PrO)_n(MO)_m NH_2]_z$
  (13) $Z[(PrO)_n(PrO\text{-}BuO)_m NH_2]_z$
  (14) $Z[(BuO)_n(EtO)_m NH_2]_z$
  (15) $Z[(BuO)_n(PrO)_m NH_2]_z$
  (16) $Z[(BuO)_n(MO)_m NH_2]_z$
  (17) $Z[(BuO)_n(PrO\text{-}BuO)_m NH_2]_z$
  (18) $Z[(MO)_n(EtO)_m NH_2]_z$
  (19) $Z[(MO)_n(PrO)_m NH_2]_z$
  (20) $Z[(MO)_n(BuO)_m NH_2]_z$
  (21) $Z[(MO)_n(PrO\text{-}BuO)_m NH_2]_z$
  (22) $Z[(PrO\text{-}BuO)_n(EtO)_m NH_2]_z$
  (23) $Z[(PrO\text{-}BuO)_n(PrO)_m NH_2]_z$
  (24) $Z[(PrO\text{-}BuO)_n(BuO)_m NH_2]_z$
  (25) $Z[(PrO\text{-}BuO)_n(MO)_m NH_2]_z$ Step III. — The product of Step II can be reacted with one of the five epoxides or mixture of oxides which had not been reacted in the immediately preceding step, i.e., either EtO, PrO, BuO, MO or PrO-BuO, with the above exclusion as to the epoxide just reacted. Further stages of oxyalkylates can be further carried out, such as Step IV, V, VI, etc.

The amino-terminated oxyalkylates are then phosphomethylolated. This is preferably carried out by the Mannich reaction as illustrated in the following reaction where

indicates at least one reactive group on the polyamine

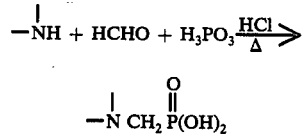

The Mannich reaction is quite exothermic and initial cooling will generally be required. Once the reaction is well under way, heat may be required to maintain refluxing conditions. While the reaction will proceed at temperatures over a wide range, i.e., from 80° to 150° C., it is preferred that the temperatures of the reaction medium be maintained at the refluxing temperatures. The reaction is preferably conducted at atmospheric pressure, although sub-atmospheric and superatmospheric pressures may be utilized if desired. Reaction times will vary, depending upon a number of variables, but the preferred reaction time is 1 to 5 hours, and the most preferred reaction time is 2½ to 3½ hours.

Although the phosphonic acid or the formaldehyde may be added in either order, or together to the reaction mixture, it is preferred to add the phosphonic acid to the amino-terminated oxyalkylate and then to slowly add the formaldehyde under refluxing conditions. Generally, about ½ to 10 moles or more of formaldehyde and about ½ to 10 moles or more of phosphonic acid can be used per mole equivalent of amine, although the most preferred molar equivalent ratios of formaldehyde:phosphonic acid:amine is 1:1:1. Excess formaldehyde and/or phosphonic acid function essentially as solvents, and thus there is no real upper limit on the amount of these materials which may be used, per mole equivalent of amine, although such excess amounts naturally add to the cost of the final product and are therefore not preferred. The preferred molar equivalent ratios are ½ to 2 moles each of the formaldehyde and phosphonic acid per mole equivalent of amine.

The Mannich reaction will proceed in the presence or the absence of solvents. The reaction may be carried out as a liquid-phase reaction in the absence of solvents or diluents, but is preferred that the reaction be carried out in an aqueous solution containing from about 40 to about 50% of the reaction monomers. Preferred conditions for the Mannich reaction include the use of formaldehyde based on the molar equivalent amount of the amine compound, the use of a stoichiometric amount of phosphonic acid based on the molar equivalent amount of amine (e.g., on the amine active hydrogen content), refluxing conditions and a pH of less than 2 and preferably less than 1.

Although formaldehyde is preferred, other aldehydes or ketones may be employed in place of formaldehyde such as those of the formula $$R-\underset{R'}{\overset{|}{C}}=O$$

where R + R' are hydrogen, or a hydrocarbon group such as alkyl, i.e., methyl, ethyl, propyl, butyl, etc., aryl, i.e., phenyl, alkylphenyl, phenalkyl, etc., cycloalkyl, i.e., cyclohexyl, etc.

The compound can also be prepared by a modified Mannich reaction by employing a chloromethylene phosphonate.

$$-\overset{|}{N}H + ClCH_2\overset{O}{\overset{\|}{P}}(OH)_2 \xrightarrow{NaOH} -\overset{|}{N}-CH_2\overset{O}{\overset{\|}{P}}(OH)_2$$

The compositions of this invention may be illustrated by the following formulae:

$$\begin{array}{c} _2(MO)\overset{O}{\overset{\|}{P}}-CH_2 \\ \phantom{xxx} \\ _2(MO)\overset{}{\overset{}{P}}-CH_2 \\ \overset{\|}{O} \end{array} \bigg\rangle N-A-(OA)_n-N \bigg\langle \begin{array}{c} CH_2\overset{O}{\overset{\|}{P}}(OM)_2 \\ \phantom{xxx} \\ CH_2\overset{}{\overset{}{P}}(OM)_2 \\ \overset{\|}{O} \end{array}$$

$$H_2C-O(AO)_n-A-N\bigg\langle \begin{array}{c} CH_2-\overset{O}{\overset{\|}{P}}-(OM)_2 \\ CH_2-\overset{}{\overset{}{P}}-(OM)_2 \\ \overset{\|}{O} \end{array}$$

$$HC-O(AO)_n-A-N\bigg\langle \begin{array}{c} CH_2-\overset{O}{\overset{\|}{P}}-(OM)_2 \\ CH_2-\overset{}{\overset{}{P}}-(OM)_2 \\ \overset{\|}{O} \end{array}$$

$$H_2C-O(AO)_n-A-N\bigg\langle \begin{array}{c} CH_2-\overset{O}{\overset{\|}{P}}-(OM)_2 \\ CH_2-\overset{}{\overset{}{P}}-(OM)_2 \\ \overset{\|}{O} \end{array}$$

where $(AO)_n$ represents the oxyalkylate group and M represents hydrogen or a salt moiety such as metals, amines, ammonia, etc.

In addition less than all of the nitrogen-banded hydrogens can be reacted so that residual NH or NH$_2$ groups may be present in the final molecule.

Suitable amino terminated oxyalkylates for use herein are manufactured and sold by Dow Chemical Company under the designation "Dow NC-1900" series. A similar series is manufactured by Jefferson Chemical Company under the designation "JEFAMINE D and T" series.

The preparation of polyoxyalkylene amino methylene phosphonic acids is illustrated by the following examples.

EXAMPLE 1

A quantity of 40 g. of Dow* NC-1990 was dissolved in 49 g. of concentrated hydrochloric acid and a 50% aqueous solution of 32.8 g. of phosphorous acid. The resulting solution was heated to reflux temperatures (100° – 110° C.) and 35.7 g. of a 37% aqueous formaldehyde solution was added dropwise over a period of one hour. After the addition was completed, the reaction mixture was kept at reflux temperature for two additional hours. A portion of this solution was evaporated in vacuo and dried in an oven. The product was a sticky solid that was soluble in water and in xylene to which a small amount of isopropanol had been added. Analysis of the IR spectra of the product indicates a polyalkylene ether terminated with amino methylene phosphonic acid groups.

*Dow NC-1990 is a polypropylene ether terminated on both ends by amine groups and having a molecular weight of 400.

EXAMPLE 2

In a similar manner, 100 g. of *"Dow NC-1992" was reacted with 16.4 g. of phosphorous acid, and 18 g. of 37% aqueous formaldehyde in the presence of 25 g. of concentrated HCl. The product when stripped of volatiles, was a pasty liquid miscible with water and soluble in xylene.

*Dow NC-1992 is a polypropylene ether terminated on both ends with amino groups and having a molecular weight of 2,000.

EXAMPLE 3

In a similar manner, 150 g. of *Dow NC-1999" was reacted with 24.6 g. of phosphorous acid, and 26.7 g. of 37% aqueous formaldehyde in the presence of 36 g. of concentrated HCl.

*Dow NC-1999 is an amino-terminated oxypropylated glycerol having a molecular weight of 3,000.

Further examples of amino-terminated polyalkylene ethers utilized in this invention are shown below.

EXAMPLE 4

Polyoxyethylene diamine (Mol. wt. of 400)

EXAMPLE 5

Polyoxyethylene diamine (Mol. wt. of 1,000)

EXAMPLE 6

Polyoxyethylene diamine (Mol. wt. of 2,000)

FORMULAE*

EXAMPLE 1

$$_2\bigg(_2(HO)\overset{O}{\overset{\|}{P}}-CH_2\bigg)N(\!-PrO\!-\!)_n-N\bigg(-CH_2-\overset{O}{\overset{\|}{P}}(OH)_2\bigg)_2$$

EXAMPLE 2

Example 1 where $n \cong 35$

EXAMPLE 3

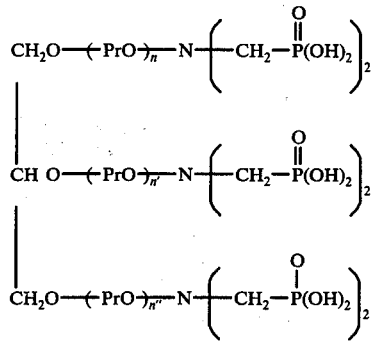

EXAMPLE 4

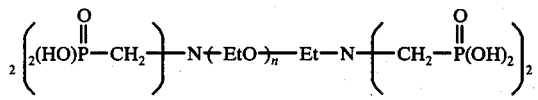

EXAMPLE 5

Example 4 where $n \cong 23$

EXAMPLE 6

Example 4 where $n \cong 46 \neq^*$ —N(PrO)$_n$N— and —N(EtO)$_n$N— is only for convenience of presenting moles of alkylene oxide, it is more properly —N(PrO)$_n$-Pr—N— and —N(EtO)$_n$Et—N—.

For convenience, some of the formulae employed herein indicate the moles of alkylene oxide employed rather than the exact linkages between the poly-oxalkylene units and the amino group, for example, H$_2$N(PrO)$_n$NH$_2$ would more properly be NH$_2$(PrO)$_n$PrNH$_2$, etc.

USE AS SCALE INHIBITOR

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 p.p.m., and are preferably used in concentrations of less than 25 p.p.m.

The compounds of the present invention (e.g., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high termperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 p.p.m. to about 50,000 p.p.m. of scale-forming salts. The compounds of the present invention effectively inhibit scale formation when present in an amount of from 0.1 to about 100 p.p.m., and preferably 0.2 to 25 p.p.m. wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 p.p.m. There is no reason to believe that this is the minimum effective concentration. The scale inhibitors of the present invention are effective in both brine, such as sea water, and acid solutions.

In the specific examples the general method of phosphomethylolation is that disclosed in Netherlands Patent 6407908 and 6505237 and in the Journal of Organic Chemistry, Vol. 31, No. 5, 1603-1607 (May, 1966). These references are hereby incorporated by reference.

In general, the method consists of the following: The amino-terminated oxyalkylate is slowly added with cooling to the mixture of phosphonic and hydrochloric acids. After the addition is completed, the reaction mixture is heated to 100°-110° C. and the aqueous formaldehyde is slowly added over a period of 1 to 1½ hours while maintaining a temperature of 100°-110°. After the addition is completed, the reaction mixture is held at reflux temperatures for 1-2 additional hours. The preferred molar equivalent ratios are ½ - 2 moles each of the formaldehyde and phosphonic acid per mole equivalent of amine, although the most preferred molar equivalent ratios of formaldehyde: phosphonic acid: amine is 1:1:1.

Calcium Scale Inhibition Test

The procedure utilized to determine the effectiveness of my scale inhibitors in regard to calcium scale is as follows:

Several 50 ml. samples of a 0.04 sodium bicarbonate solution are placed in 100 ml. bottles. To these solutions is added the inhibitor in various known concentrations. 50 ml. samples of a 0.02 M CaCl$_2$ solution are then added.

A total hardness determination is then made on the 50—50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

Table II describes the scale inhibition test results obtained.

TABLE II

Inhibition of Scale Formation from a CaCO$_3$ Solution at 180° F. for 4 hours. (200 p.p.m. CaCO$_3$).

| Inhibitor | Salt | Conc. (ppm) | Percent Scale Inhibition |
|---|---|---|---|
| Example 1 | H | 50 | 60 |
| Example 1 | Na | 50 | 54 |
| Example 2 | H | 50 | 36 |
| Example 3 | H | 50 | 39 |
| Example 4 | H | 50 | 59 |
| Example 4 | Na | 50 | 53 |
| Example 5 | H | 50 | 42 |
| Commercial Phosphonate Scale Inhibitor | Na | 50 | 40 |
| Commercial Organic Phosphate Scale Inhibitor | Na | 50 | 35 |

The salt moiety can vary widely to include any suitable metal, ammonia, amine, etc., cation such as an alkali metal, i.e., sodium, potassium, etc., a monoamine such as methyl amine, ethyl amine, etc., poly amines such as ethylene diamine, propylene diamine, the corresponding polyamines such as diethylene triamine, triethylene tetramines, etc.; alkanolamines such as ethanolamine, diethanolamine, propanolamines, etc.; cyclicamines such as piperidine, morpholine, etc. Thus, any salt moiety capable of carrying out this invention can be employed.

USE IN THE CHELATION OR SEQUESTRATION OF METAL IONS

The chelating or sequestering agents of the present invention are of wide utility such as when it becomes necessary to sequester or inhibit the precipitation of metal cations from aqueous solutions. Among their many uses are the following applications:

Soaps and detergents, textile processing, metal cleaning and scale removal, metal finishing and plating, rubber and plastics, industry, pulp and paper industry, oilwell treatment, chelation in biological systems.

An important function of these compounds is their ability to sequester $Fe^{+2}$. In secondary oil recovery by means of water floods, waters are frequently mixed on the surface prior to injection. Frequently these waters contain amounts of $Fe^{+2}$ and $H_2S$. If these incompatible waters are mixed, an FeS precipitate results which can plug the sand face of the injection well. Another of their functions is to prevent formation of gelatinous iron hydroxides in the well and in the effluent production waters.

To demonstrate the effectiveness of the methylene phosphonates of amino-terminated oxyalkylates in chelating $Fe^{+2}$, the following test procedure was utilized. Into a flask that contained a known concentration of the sequestering agent, and enough sodium hydroxide or hydrochloric acid to give the desired pH was placed a 100 ml. aqueous sample of ferrous ammonium sulfate (20 ppm of $Fe^{+2}$) after final pH adjustment the solution was allowed to remain at ambient temperatures for 48 hours. The solution was centrifuged for one hour to remove collodial iron hydroxide and an aliquot of the supernatant solution was analyzed by atomic absorption to determine the iron concentration.

The following table illustrates the ability of the sequestering agents of the present invention to sequester $Fe^{+2}$, as compared to the well known sequestering agent tetrasodium ethylenediamine tetra-acetate (EDTA).

TABLE III

| pH | Sequestering Agent (ppm) Product Example | Amount of iron Sequestered (ppm) |
|---|---|---|
| 5 | 1 (50) | (12) |
| 5 | 2 (50) | (9) |
| 5 | 3 (50) | (7) |
| 5 | EDTA (50) | (7) |
| 7 | 1 (50) | (12) |
| 7 | 2 (50) | (9) |
| 7 | 3 (50) | (7) |
| 7 | EDTA (50) | (7) |
| 10 | 1 (150) | (9) |
| 10 | 2 (150) | (7) |
| 10 | 3 (150) | (6) |
| 10 | EDTA (150) | (6) |

As one can observe from the preceding table the sequestering agents of this invention are as effective, and in some cases superior, to EDTA when tested over a wide pH range.

The sequestering agents of this invention are also quite effective in sequestering other metal cations in aqueous solutions. For example, a test was conducted in which 60 ppm of the sequesterant were dissolved in 100 ml. of water. The pH was adjusted to 9 and maintained there. Metal cations were added, in the following amounts, before a noticeable precipitate was formed.

TABLE IV

| Sequesterant Product | Metal (ppm) Sequestered per 60 ppm of Sequesterant | |
|---|---|---|
| Example 1 | $Fe^{+3}$ | (60) |
| Example 1 | $Al^{+3}$ | (120) |
| Example 1 | $Cu^{+2}$ | (120) |
| Example 1 | $Ni^{+2}$ | (50) |
| Example 2 | $Fe^{+3}$ | (40) |
| Example 2 | $Al^{+3}$ | (80) |
| Example 2 | $Cu^{+2}$ | (60) |
| Example 2 | $Ni^{+3}$ | (40) |

Other heavy metals sequestered by the sequestering agents of this invention such as cobalt, manganese, chromium and the like.

The amount employed to chelate is controlled by stoichiometry in contrast to scale inhibition where the amount employed is threshold or less than stoichiometric.

In summary, the products of this invention are phosphomethylolated amino-terminated oxyalkylates having at least two amino groups. The oxyalkylate group is preferably derived from ethylene oxide, propylene oxide or butylene oxide, but most preferably from ethylene oxide or propylene oxide or combinations thereof, and has from about 3 to 150 or more oxyalkylate units, such as from about 5 to 100 units, but preferably from about 8 to 75 units. The phosphomethylolated groups, i.e.,

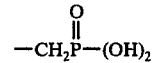

(or salts thereof) are substituted for at least 50% such as at least 75% but preferably 90–100% of the available nitrogen-bonded hydrogens on the amino-terminated oxyalkylates. The preferred amino-terminated oxyalkylate employed have a molecular weight of about 100 to 5,000 such as from about 250 to 4,000, but preferably from about 200 to 3,000.

These compositions are employed as scale inhibitors, chelating agents, and the like. They are particularly useful as metal ion sequestrants and threshold scale inhibitors as well as having desirable surface active properties. They also have the property of being water soluble or dispersible as well as being soluble in organic solvents. The compounds of this invention can also find utility in such fields as water treating agents, detergents, metal cleaning, corrosion inhibitors, emulsifiers, breaking or preventing petroleum emulsions, oil additives, gasoline additives, lubricants, and the like.

Having thus described my invention, what I claim as new and desire by Letters Patent is:

1. Methylene phosphonates of amino-terminated oxyalkylates having at least 2 amino groups, said oxyalkylates being of the formula

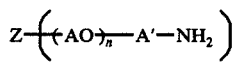

where Z is the oxyalkylated base of a base oxyalkylatable compound selected from the group consisting of polyhydric alcohols, polyhydric ether alcohols, polyhydric phenols and phenol aldehyde resins, (AO)$_n$ is ethylene oxide, propylene oxide, butylene oxide, amylene oxide, octylene oxide, styrene oxide, methylstyrene oxide, cyclohexene oxide or combinations thereof, A' is an alkylene group, n is about 3 to 150 and z is at least 2, the methylene phosphonates having at least 2 terminal groups of the structure

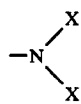

where X is hydrogen or

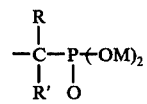

with the proviso that less than all of the Xs in said terminal groups may be

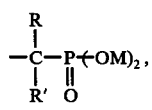

each of the R and R' groups being hydrogen, alkyl, aryl or cycloalkyl, M being hydrogen, metal or ammonia.

2. The methylene phosphonates of claim 1 where (AO)$_n$ is ethylene oxide, propylene oxide or butylene oxide or combinations thereof.

3. The methylene phosphonates of claim 2 where (AO)$_n$ is ethylene oxide, propylene oxide or combinations thereof.

4. The methylene phosphonates of claim 3 where the formula is

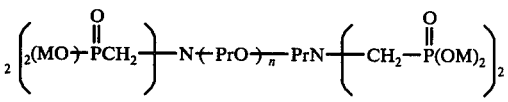

where $n \cong 7$ or 35 and M is hydrogen or Na.

5. The methylene phosphonate of claim 4 where the formula is

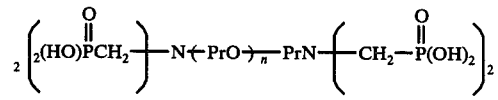

where $n \cong 7$.

6. The methylene phosphonate of claim 3 where the formula is

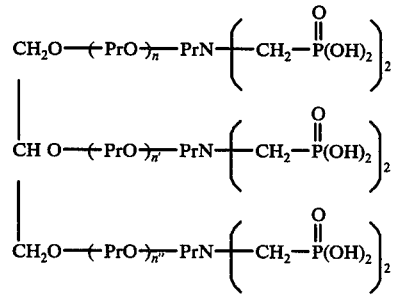

where $n + n' + n'' \cong 52$.

7. The methylene phosphonates of claim 3 where the formula is

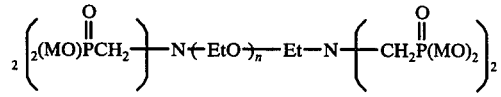

where $N \cong 9$, 23 or 46 and M is hydrogen or Na.

8. The methylene phosphonate of claim 6 where the formula is

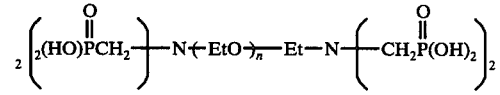

where $n \cong 9$.

9. The methylene phosphonate of claim 1 where M is hydrogen alkali metal or ammonia.

* * * * *